United States Patent [19]

Buhler

[11] 4,054,670

[45] Oct. 18, 1977

[54] SKIN-TREATING COMPOSITION CONTAINING POLYSILOXANE FLUIDS

[75] Inventor: Allen C. Buhler, Racine, Wis.

[73] Assignee: Growth Products, Inc., Racine, Wis.

[21] Appl. No.: 584,139

[22] Filed: June 5, 1975

Related U.S. Application Data

[63] Continuation-in-part of Ser. No. 223,711, Feb. 4, 1972, abandoned.

[51] Int. Cl.$^2$ .................................... A61K 47/00
[52] U.S. Cl. .................................... 424/358; 424/168; 424/366
[58] Field of Search ........................ 424/365, 358

[56] References Cited

U.S. PATENT DOCUMENTS 3,240,670  3/1966  Femberg .................... 424/172 X

FOREIGN PATENT DOCUMENTS

| 564,417 | 10/1958 | Canada | 260/29.2 M |
| 1,069,982 | 2/1954 | France | 424/189 |
| 1,161,000 | 3/1958 | France | 424/184 |
| 1,218,536 | 12/1959 | France | 424/184 |
| 1,241,560 | 1/1962 | Germany | 424/184 |
| 476,120 | 1/1952 | Italy | 424/184 |

OTHER PUBLICATIONS

Ron Coming, New Products Information, 7/8/70, pp. 1 to 7.

Primary Examiner—Dale R. Ore

[57] ABSTRACT

A skin-treating and protecting composition which forms an air-permeable, protective barrier contains an emulsifying agent, one or more emollients and a major portion by weight of water. The critical ingredients are a combination of up to 10% by weight of dimethyl/trimethyl polysiloxane fluid and at least one part by weight of dimethyl polysiloxane fluid to each four parts of the dimethyl/trimethyl polysiloxane fluid.

1 Claim, No Drawings

SKIN-TREATING COMPOSITION CONTAINING POLYSILOXANE FLUIDS

CROSS REFERENCE TO RELATED APPLICATION

This application is a continuation in-part of Ser. No. 223,711, filed Feb. 4, 1972, now abandoned.

BACKGROUND OF THE INVENTION

1. Field of Use

This present invention relates to a composition for protecting and treating the skin. More specifically, it relates to a composition which, when applied to the skin of the hands, for example, dries to form a flexible, invisible protective barrier.

2. Description of the Prior Art

Skin on the hands, particularly the palms, is kept soft by a fatty lubricating matter, sebum, which is secreted by the sebaceous glands in the skin. When the hands are exposed to dry, cold air, an insufficient supply of sebum is exuded, resulting in cracking or chapping of the skin. Then, too, alkyl aryl sulphonates, phosphates and other chemicals usually found in detergents, are highly lipophilic, destroying the natural oils and contributing to the roughness of the skin.

Many compositions have been made commercially available which are designed to remedy roughness and cracking of the skin. All such compositions contain emollients, fatty acid esters or mineral oil which are intended to at least partially alleviate the condition by manually rubbing the compound into the skin. Other compositions have been taught which include, for more severe cases, a pyroxylin solution.

Although dimethyl silicones have been accepted as possessing recognizable water-repelling characteristics in other applications, such as for mill use in the manufacture of fabrics, they have not performed adequately as a barrier when applied to the skin. Collodion, or pyroxylin solutions operate as a temporary air-tight seal for burns, but cannot be used as a day-to-day application to the hands to prevent common roughness or chapping.

SUMMARY OF THE INVENTION

A skin-treating and skin-protecting composition in accordance with the present invention includes dimethyl/trimethyl polysiloxane and dimethyl polysiloxane. The preferred composition comprises at least one part by weight of dimethyl polysiloxane to each four parts of dimethyl/trimethyl polysiloxane. The composition in a preferred lotion form comprises approximately 2 percent to 10 percent by weight of dimethyl/trimethyl polysiloxane and at least one part by weight of dimethyl polysiloxane to each four parts of said dimethyl/trimethyl polysiloxane. Preferably, the balance of the lotion is principally a diluent such as water with an emulsifying agent and one or more emollients.

The composition upon application to the skin, forms an air-permeable, invisible barrier to protect the skin from the elements or materials which cause dryness and chapping. Furthermore, the composition dries readily, is non-tacky and completely flexible, and also renders the skin softer and more pliable.

A composition in accordance with the invention comprises and possesses features, properties, and a relations of constituents, which are exemplified in the following detailed description, and the scope of the invention will be indicated in the claims.

DESCRIPTION OF A PREFERRED EMBODIMENT

A skin-treating and protecting composition in the form of a lotion in accordance with the invention comprises a major portion by weight of water, one or more emollients and emulsifying agent, the combination of up to 10 percent by weight of dimethyl/trimethyl polysiloxane and at least one part of dimethyl polysiloxane to four parts of said dimethyl/trimethyl polysiloxane.

It has been discovered that a unique polysiloxane fluid, dimethyl/trimethyl, has outstanding barrier properties for application to the skin when formulated with other critical ingredients. This silicone fluid, dimethyl/trimethyl polysiloxane, may be described as a trimethyl resin dissolved in and reacted with dimethyl fluid. The conventional dimethylpolysiloxane chain, has trimethyl siloxy groups on each end of the chain, blocking it from further reaction. The dimethyl/trimethyl fluid has a 50—50 ratio of dimethyl groups, $ME^2SiO$, and trimethyl groups, $ME^3SiO$. Apparently, it is this unique balance of the two groups that results in the extremely high water-resistance the fluid dimethyl/trimethyl siloxane imparts. The dimethyl/trimethyl polysiloxane is water-white in color and has a viscosity at 25° C of from 500–750 centistokes, a flash point of 570° F, a refractive index at 25° C of 1.4080 and a specific gravity at 25° C of 1.034.

As hereinbefore mentioned, dimethyl silicone fluid is known to possess limited water-repelling characteristics and has not performed adequately or satisfactorily when used as a moisture barrier when applied to the human skin. Dimethyl silicone fluid has a chain comprised entirely of $ME^2SiO$ groups with one trimethyl group on each end.

However, it has been found through experimentation that this particular fluid, dimethyl/trimethyl polysiloxane, can be combined with a dimethyl polysiloxane to provide a composition surprisingly well-suited for skin application. The dimethyl/trimethyl fluid is preferably incorporated in a range of from 2 to 10% by weight. In such a skin-treating composition, less than 2 percent by weight of the dimethyl/trimethyl polysiloxane is insufficient to offer the water-resistance needed. More than 10 percent by weight is superfluous since more than that proportion does not offer any additional protection.

However, the dimethyl/trimethyl polysiloxane fluid, when used in the prescribed amounts in a composition not containing dimethyl polysiloxane, tends to give the skin an unpleasant burning sensation or astringent effect. It has been found that the incorporation of critical proportions of dimethyl fluid is unique in completely eliminating the burning sensation or undesirable astringent effect. Ideally, the viscosity of both fluids falls within a range of from 200 to 1000 centistokes. Exceeding that range does not necessarily detract from the efficacy of the compound, but the composition is viscous and more difficult to apply.

The compound in accordance with the present invention in the form of a lotion contains a major portion by weight of water and a suitable emulsifying agent. Emulsifying agents typically used in connection with known creams and lotions are operable. For example, any of the fatty acids, generally having from 10 to 20 carbon atoms are acceptable when combined with an amine, such as triethanolamine, ethanolamine, or morpholine, or potassium hydroxide. I prefer to use triethanolamine stearate. The stearic acid should be incorporated within a range of from 1 percent to 6 percent by weight. Less than 1 percent is inadequate, whereas more than 6 percent will result in a product which is too greasy and not free-flowing. About 2 percent weight of triethanolamine is preferred. If more than that amount is used the product becomes less and less viscous, taking on a watery consistency.

One or more typical emollients are also used in the lotion such as lanolin, glycerol, glycerol monostearate, oleic acid, a sorbitol and mineral oil. I have found that mineral oil and cetyl alcohol to be the preferred combination, the latter not only contributing to the mollifying effect on the lotion, but promoting a smooth opacity to the liquid.

The following is an example of the steps in formulating a compound in accordance with the invention in the form of a lotion.

Stearic acid, triple-pressed, in the amount of 3 percent by weight of the total formulation was combined with 4 percent of dimethyl/trimethyl polysiloxane, 2 percent of dimethyl polysiloxane, and 1 percent of cetyl alcohol. The mixture was heated to 70° C.

In another vessel 1.5 percent by weight of triethanolamine, 0.1 percent of preservative (parahydroxy benzoate) and 86.4 percent of water was admixed. The mixure was heated to 70° C and the contents of the first vessel were added to it while stirring on a propeller type agitator. The total mass was cooled with continued stirring. At 120° F perfume and coloring were added. The product is packaged after the temperature is decreased to les than 100° F.

When applied to the skin the water-repellancy of this formulation far surpasses all cosmetic compositions known to date which depend upon a silicone fluid for repellancy.

The inclusion of dimethyl fluid allows the dimethyl/trimethyl fluid to perform but uniquely eliminates the otherwise burning or tingling sensation.

There are several types of testing which indicate the high degree of protection afforded the skin by this composition. In one such type of test a drop of ink is placed on the skin in two different spots. The ink is allowed to dry, and then the protective lotion is applied over one of the spots. After allowing about twenty minutes for the lotion to dry, the ink spots are washed with a bar of soap and water. The ink spot, coated with the composition of the instant invention, is extremely difficult to remove when compared to the effort needed to remove the other ink spot. This is also true when the "other ink spot" is first coated with conventional silicone formulations.

RESUME

A skin-treating and skin-protecting composition, in accordance with the present invention in lotion form comprises dimethyl/trimethyl polysiloxane, dimethyl polysiloxane, an emulsifying agent, one or more emollients, and a diluent such as water. A preferred composition in the form of a lotion comprises approximately 2 percent to 10 percent by weight of dimethyl/trimethyl polysiloxane and at least one part by weight of dimethyl polysiloxane to each four parts of said dimethyl/trimethyl polysiloxane, the balance being emollient, emulsifying agent and diluent such as water. Preferably, the total composition comprises a major portion by weight of a diluent such as water.

I claim:

1. In a cosmetic composition for application to the skin to form an air-permeable, invisible, protective barrier thereon, containing one or more emollients, an emulsifying agent and a major portion by weight of water, the improvement which comprises incorporating in said composition the combination of dimethyl/trimethyl polysiloxane fluid, said fluid being present in a quantity of not less than 2% and not more than 10% by weight, and at least one part dimethyl polysiloxane fluid, present for each four parts of said dimethyl/trimethyl polysiloxane fluid.

* * * * *